US005696805A

United States Patent [19]
Gaborski et al.

[11] Patent Number: 5,696,805
[45] Date of Patent: Dec. 9, 1997

[54] APPARATUS AND METHOD FOR IDENTIFYING SPECIFIC BONE REGIONS IN DIGITAL X-RAY IMAGES

[75] Inventors: Roger Stephen Gaborski, Pittsford; Thaddeus Francis Pawlicki, Rochester, both of N.Y.

[73] Assignee: Eastman Kodak Company, Rochester, N.Y.

[21] Appl. No.: 713,683

[22] Filed: Sep. 17, 1996

[51] Int. Cl.⁶ .......................... G01N 23/04; G01N 23/02
[52] U.S. Cl. ................................. 378/54; 378/56
[58] Field of Search ..................... 378/54, 55, 56

[56] References Cited

U.S. PATENT DOCUMENTS

| | | | |
|---|---|---|---|
| 4,721,112 | 1/1988 | Hirano et al. | 128/659 |
| 5,335,260 | 8/1994 | Arnold | 378/207 |
| 5,365,564 | 11/1994 | Yashida et al. | 378/56 |

*Primary Examiner*—David P. Porta
*Assistant Examiner*—David Vernon Bruce
*Attorney, Agent, or Firm*—William F. Noval

[57] ABSTRACT

A method of automatically segmenting the bone regions in a digital radiograph of a body extremity comprising the steps of: providing a digital radiographic image of a body extremity having one or more digits; estimating the upper and lower threshold values of the provided image; binarizing the provided image by a binarization system which uses the estimated upper and lower threshold values to produce a bi-tonal image; removing noise from the binarized image by a noise removal system; processing the noise removed binary image by a skeletonization technique in order to form an initial estimate of the central axis of each body extremity digit; approximating the locus of points generated by the processing step by a linear fit system; joining lines with near end points with a line linking system which results in a piece wise linear approximation of the central axis for each body extremity digit; for each point along the axes, generating perpendicular projections which extend a fixed pixel distance; for each perpendicular projection, averaging the pixel values by a trace generation system; convolving each density trace with a matched filter; analyzing the output of the matched filter step by a joint detection system to locate digit joints; for each body extremity digit, determining the bone edges between two joints; and determining the average density of the digit region between the digit joints and bone edges.

10 Claims, 10 Drawing Sheets

APPARATUS AND METHOD FOR IDENTIFYING SPECIFIC BONE REGIONS IN DIGITAL X-RAY IMAGES

FIELD OF INVENTION

This invention is broadly directed to the field of digital image processing systems. A primary application of the invention relates to the processing of digital x-ray images. A specific example of this primary application is the automatic identification of regions corresponding to phalanx bones in digitized dorso-palmer views of hand radiographs.

BACKGROUND OF THE INVENTION

The current interest in the determination of bone mass reflects the recognition of the physiological importance of bone, with its wide range of functions (Non-Invasive Measurements of Bone Mass and Their Clinical Application, Cohn, S. H., Ed. CRC Press, 1981). Bone is a particularly interesting tissue to study. Unlike soft tissue, it imprints and then retains, for long periods, evidence of events experienced by the organism through changes in its morphology, and in its physical and chemical properties. The high mineral content of the bone makes it amenable to study by means of non-invasive radiological techniques which measure the bone density.

Price (Price, W. A., The Science of Dental Radiology, Dent. Cosmos, 43, 483, 1901) was among the first investigators who successfully measured bone mineral from the x-ray image. In the first half of this century, a visual image of bone, obtained by radiography, was used to study bone morphology. Changes in bone mass in individuals with such conditions as osteoporosis can be visually observed with this technique. Over time, a number of refinements have been introduced to the basic technique. Significant improvements have been made in x-ray sources and in the films used. Photodensitometric techniques have increased the sensitivity of the measurement systems.

The study of bone mass and the changes with age, various diseases, and metabolic disorders is of primary importance for diagnosis and treatment. One of the most widespread disorders is the loss of bone mass that is normal concomitant of aging among all peoples. The condition, however, is most severe in postmenopausal Caucasian women. It is estimated that the chronic debilitating condition, osteoporosis, which results in crush fractures of the spine and trauma fractures of other weight-bearing bone as the bone becomes increasingly fragile, affects at least five million women in the U.S. alone. While no threshold level of bone mass (corrected for body habitus, sex, and age) has been firmly established for the identification of osteoporotic individuals, it is nevertheless possible to identify a population at risk.

The reduction in bone mass, the essential feature of osteoporosis, results from an imbalance between the rate of formation of bone and the rate of reabsorption. There are a variety of diseases and conditions for which measurement of bone mass is useful in both diagnosis and therapy. Management of calcium level of the growing group of renal patients receiving hemodialysis is made more effective with measurement of total body calcium. Diseases such as osteogenesis imperfecta, Paget's disease, Cushing's syndrome, diabetes mellitus, alcoholism, and thalassemia, have all utilized measurements of bone one technique or another.

Radiographic absorptiometry (Colbert, C., The Osseous System, and Overview, Invest. Radiol., 7 223, 1972; Meema, H. E. and Meemas, S., The Interrelationship Between Cortical Bone Thickness, Mineral Mass and Mineral Density in Human Radius: A Roentgenologic-Densitometric Study, in Progress in Methods of Bone Mineral Measurement, Whdon, G. D. and Cameron, J. R., Eds., U.S. Department of Health, Education and Welfare, Bethesda, Md., 1970, 135; Colbert, C., Radiographic Absorptiometry, Ph.D. Thesis, Union Graduate School, Cincinnati, Publ. 79-3507, Microfilms International, 1978) or photodensitometry, is a sensitive, noninvasive, quantitative method used to assess bone mineral changes. In such systems, the x-ray image is divided into an array of cells (pixels), each of which has a distinctive optical density (gray level). A computer-controlled densitometer scans the x-ray image with a light beam, and the data are analyzed by computer for the determination of bone mineral density.

As hospital x-ray procedures may vary widely, it is deemed necessary to compensate for variations is kilovoltage, exposure, and film processing procedure. The correction term are derived from pixel data take from a scan of a reference wedge image. This reference wedge is located next to the body part imaged by the x-ray.

Changes in the phalangeal bones are often used as indicators of systemic bone disease (Kerr, D. N. S., Walls, J., Ellis, H., Simpson, W., Uldall, P. R., and Ward, M. K., Bone Disease in Patients Undergoing Regular Hemodialysis, J. Bone Jt. Surg., 51B, 578, 1969). Thus, one of the principal modalities of diagnostic procedure is the determination of the mineral content of the phalanges. The values obtained are compared with age and sex matched peer norms.

Lightly exposed radiographs of the hand-wrist are used so that there is no radiation exposure to the axial skeleton. No special x-ray procedures are required except that of the placement of the wedge alongside the index finger. For patients up to age 20 for whom serial radiographs are made, a report on phalageal bone size compared with age and sex matched norms is provided as an indicator of growth.

A major problem and operational bottle neck in RA measurement involves locating the phalanx region in a hand image. This is usually performed by having a skilled operator position and delimit the region of interest on a microdensitometer (see, e.g., U.S. Pat. Nos. 3,339,734; 3,665,419; 3,673,394; 4,721,112; 4,829,549; 4,903,203; and Japanese Patent publication 01-158941 (1989)).

SUMMARY OF THE INVENTION

According to the present invention, there is provided a solution to the problems of the prior art.

According to a feature of the present invention, there is provided a method of automatically segmenting the bone regions in a digital radiograph of a body extremity comprising the steps of:

providing a digital radiographic image of a body extremity having one or more digits;

estimating the upper and lower threshold values of the provided image;

binarizing the provided image by a binarization system which uses the estimated upper and lower threshold values to produce a bi-tonal image;

removing noise from the binarized image by a noise removal system;

processing the noise removed binary image by a skeletonization technique in order to form an initial estimate of the central axis of each body extremity digit;

approximating the locus of points generated by the processing step by a linear fit system;

joining lines with near end points with a line linking system which results in a piece wise linear approximation of the central axis for each body extremity digit;

for each point along the axes, generating perpendicular projections which extend a fixed pixel distance;

for each perpendicular projection, averaging the pixel values by a trace generation system;

convolving each density trace with a matched filter;

analyzing the output of the matched filter step by a joint detection system to locate digit joints;

for each body extremity digit, determining the bone edges between two joints; and determining the average density of the digit region between the digit joints and bone edges.

ADVANTAGES EFFECT OF THE INVENTION

An object of this invention is to provide a system for automatically delimiting or segmenting regions corresponding to the phalanx bones in digitally scanned images of hand radiographs.

It is also an object of this invention to provide a system for the automatically delimiting or segmenting regions corresponding to the reference wedge in a digitally scanned image containing such a wedge.

It is a further object of this invention to provide a system able to quantitatively measure the bone density of phalanx bones using the information gained through the segmentation of phalanx bones and reference wedges.

DETAILED DESCRIPTION OF THE INVENTION

Figure 10:
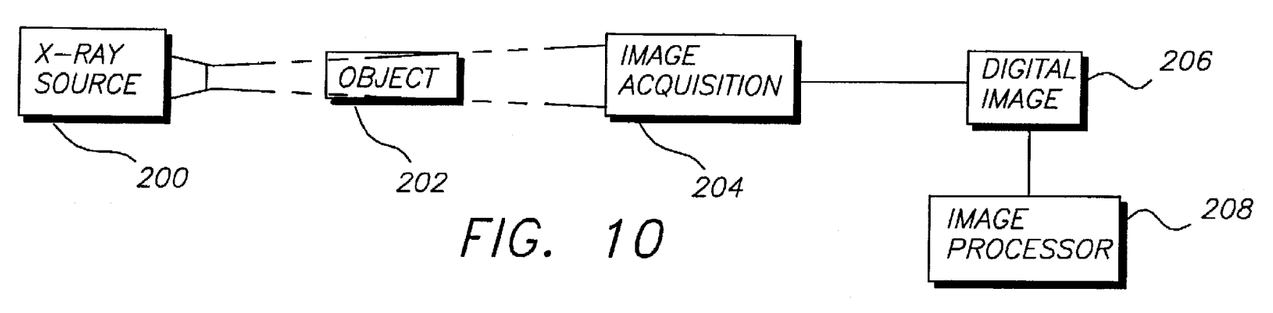
FIG. 10 is a block diagram of a digital image acquisition system.

The method of the present invention is described as a series of operations performed on a digital image of a body part extremity having digits (e.g., a hand with fingers). The digital image can be formed by the digital image acquisition system of FIG. 10. As shown, x-ray source 200 projects x-rays through object 202 (such as a body part extremity, e.g., hand or foot) to image acquisition system 204. The image acquisition system can be, for example, (1) a standard x-ray screen/film combination which produces an x-ray film image which is processed chemically or thermally and the processed film digitized by a scanner/digitizer 206; (2) a computed radiography system where a latent x-ray image is formed in a storage phosphor 204 and a corresponding digital image is produced by reading out the storage phosphor by a CR reader 206; (3) a diagnostic scanner (such as MRI, CT, US, PET) produces an electronic x-ray image which is digitized; and (4) a direct digital acquisition system typically consisting of a phosphor based scintillating screen coupled to an imager (cap, mos) through a lens or fiber optic system.

Figure 11:
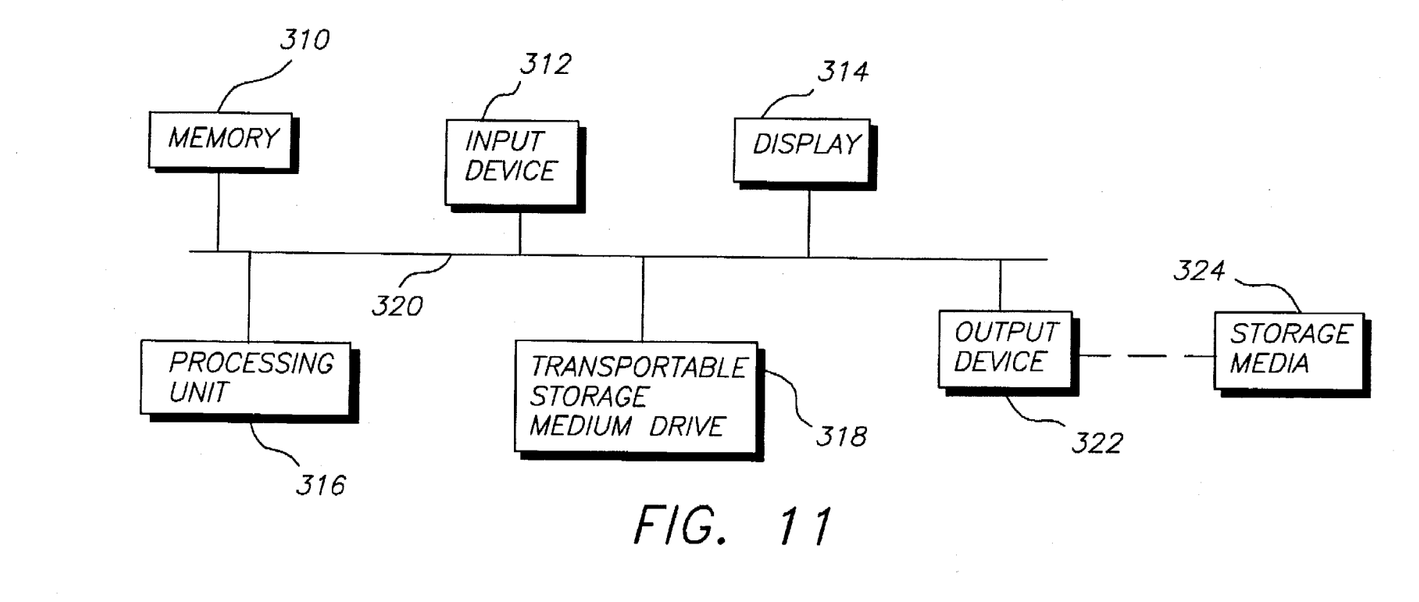
FIG. 11 is a block diagram of an image processor for carrying out the method of the present invention.

The digital image is processed in image processor 208, according to the method of the present invention. Image processor can take the form of a digital computer, such as illustrated in FIG. 11. In such case, one or more of the steps of said method can be carried out using software routines. Image processor can also include hardware or firmware for carrying out one or more of said method steps. Thus, the steps of the method of the invention can be carried out using software, firmware, and hardware, either alone or in any preferable combination.

As shown in FIG. 11, a digital computer 300 includes a memory 310 for storing digital images, application programs, operating system, etc. Memory 310 can include mass memory (such as a hard magnetic disc or CD ROM), and fast memory (such as RAM). Computer 30 also includes input device 312 (such as a keyboard, mouse, touch screen), display 314 (CRT monitor, LCD), central processing unit 316 (microprocessor), output device 318 (thermal printer, dot matrix printer, laser printer, ink jet printer). Components 310, 312, 314, 316, and 318 are connected together by control/data bus 320. Computer 300 can include a transportable storage medium drive 322 for reading from and/or writing to transportable storage media 324, such as a floppy magnetic disk or writeable optical compact disk (CD).

As used in this application, computer readable storage medium can include, specifically, memory 310 and transportable storage medium 324. More generally, computer storage medium may comprise, for example, magnetic storage media, such as magnetic disk (hard drive, floppy disk)

or magnetic tape; optical storage media, such as optical disk, optical tape, or machine readable bar code; solid state electronic storage devices, such as random access memory (RAM), read only memory (ROM); or any other physical device or medium which can be employed to store a computer program.

Figure 1:
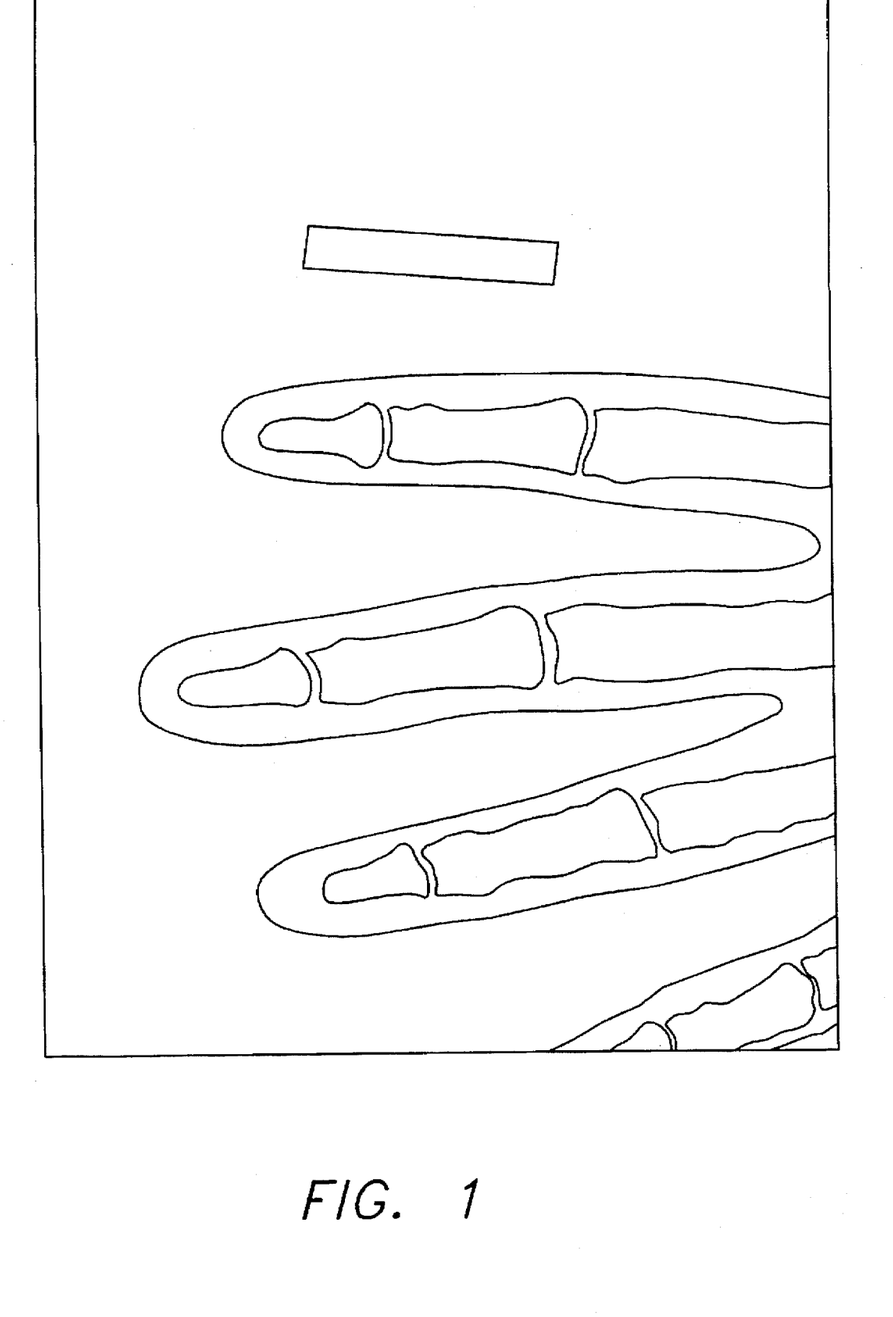
FIG. 1 shows a diagrammatic-view of the typical monochrome gray scale x-ray input image. It clearly shows an x-ray image of four fingers. The notched rectangle is the standard wedge used for calibration purposes.
Figure 8:
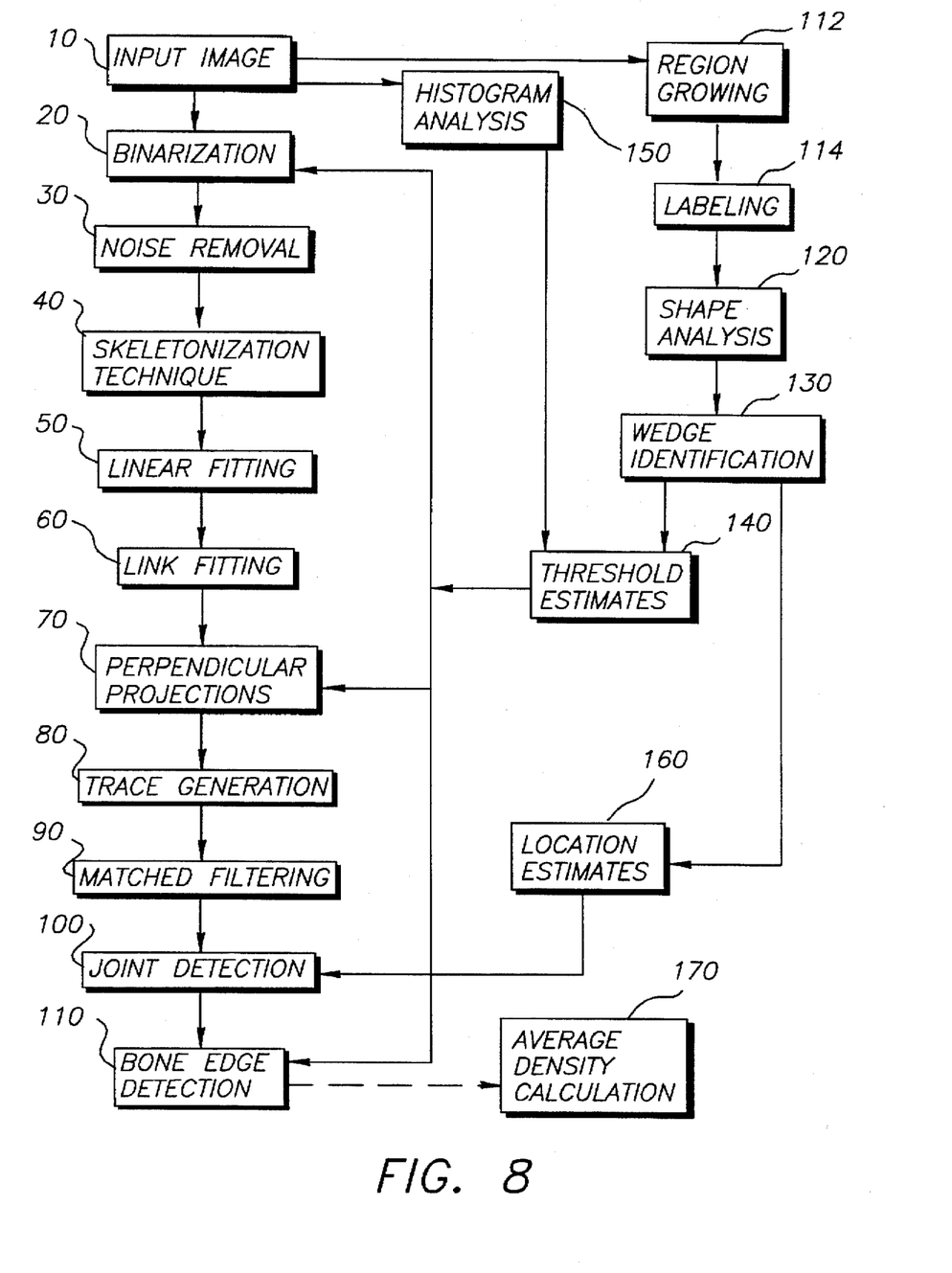
FIG. 8 shows in block diagram form the major method steps of the invention.

The major portions of the invention described below is depicted in block diagram form by FIG. 8. Input to the system is a digital image (Block 10). The output, or end result of the system is an image depositing the regions corresponding to the phalangeal bones and the standard wedge found in that image. An example of the type of image used as input (Block 10) is depicted in FIG. 1.

Figure 9:
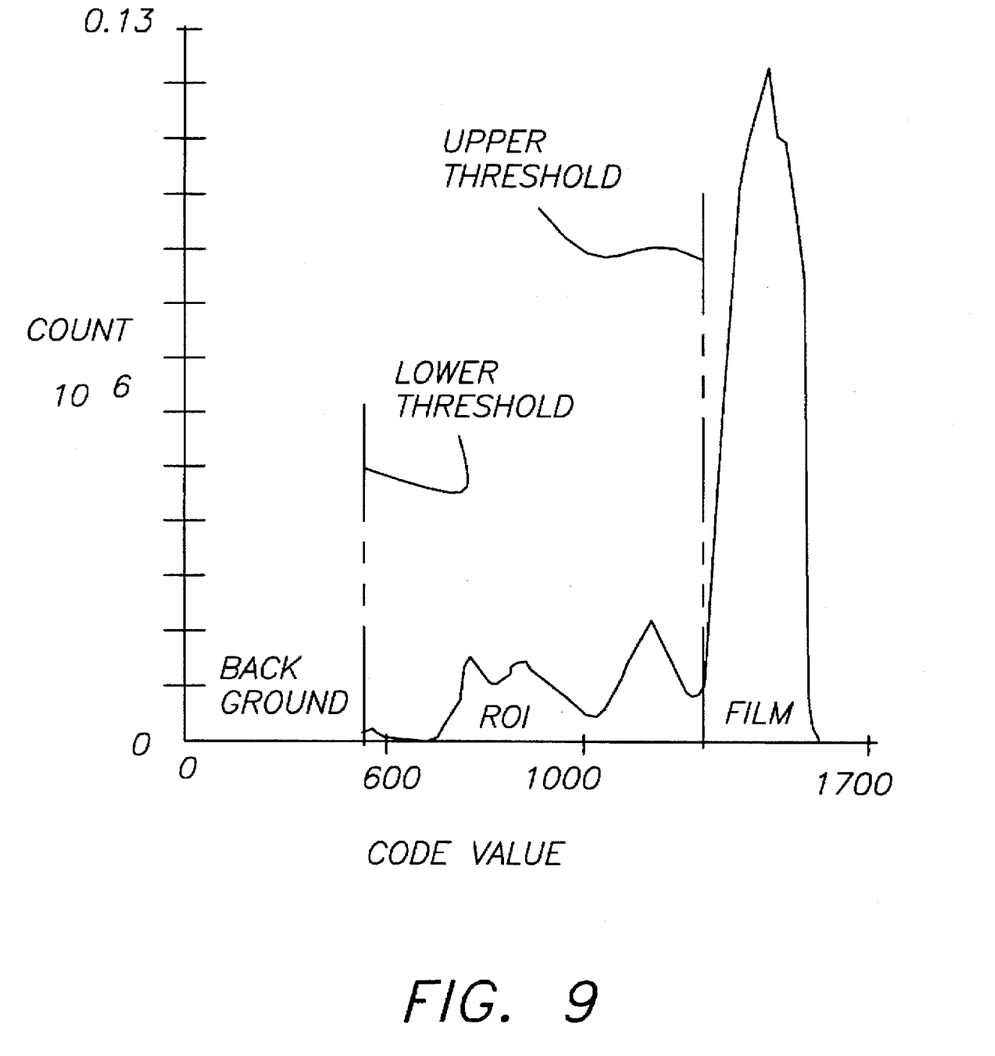
FIG. 9 shows a graphical view of a characteristic histogram of a hand image. The large distribution of pixels to the right of the upper threshold point correspond to those regions of the image where blank film has been scanned. The small distribution to the left of the lower threshold correspond to those regions of the image where foreground objects exist (usually scanned areas that contain no film). The distribution in between the lower threshold value and the upper threshold value constitutes the region of interest (ROI) of the image. The characteristic nature of this histogram facilitates determination of the upper and lower threshold values.

A frequency density histogram is generated for the input image and analyzed by a Histogram Analysis system (Block 250). Typically, x-rays images of the type processed by this system have a characteristic histogram. FIG. 9 shows the histogram of the image from FIG. 1. A large distribution to the left of the upper threshold value corresponds to the region of image depicting blank film. The small distribution to the left of the lower threshold typically corresponds to background regions where the scanner or microdensitometer found no film. The region of interest (ROI) is found in between the lower and upper threshold values. The upper threshold value can be quickly determined with reasonable accuracy by finding the valley of the histogram just below the right most peak. The lower threshold value can be quickly determined with reasonable accuracy by finding the valley just above the zero code value.

Upper and lower threshold values can also be accurately estimated as a function of the minimum and maximum code values found in the region of the image corresponding to the standard wedge. The location of the standard wedge can be reliably determined because it is typically surrounded blank film region. To do this, the input image (Block 10) is analyzed through a splitting and merging region growing algorithm (Block 112). Each unique region generated by the region growing system is given a laser by a labeling system (Block 114). Each labeled region is subject to shape analysis (Block 120). In the preferred embodiment, three parameters are used to analyze shape. The first parameter is expected size (pixel area) of the wedge. The second parameter is the expected eccentricity of the region. The third parameter is expected distance from the center of the image. The calculated value of each of these parameters for each labeled region is passed to the wedge identification system (Block 130). Probability distributions can be calculated for each of the parameters and the region that best matches all three constraints is selected as the standard wedge. Once this region is selected, minimum and maximum pixel values found within this region are used to estimate the upper and lower threshold values used in the binarization system (Block 20).

In the preferred embodiment estimates from both histogram analysis (Block 150) and wedge identification (Block 130) are combined by the threshold estimation system (Block 140) to determine optimal values for the upper and lower thresholds. Currently, a weighted average of the two estimates is used. If the estimates from the two systems vary widely, error condition is signaled.

Figure 2:
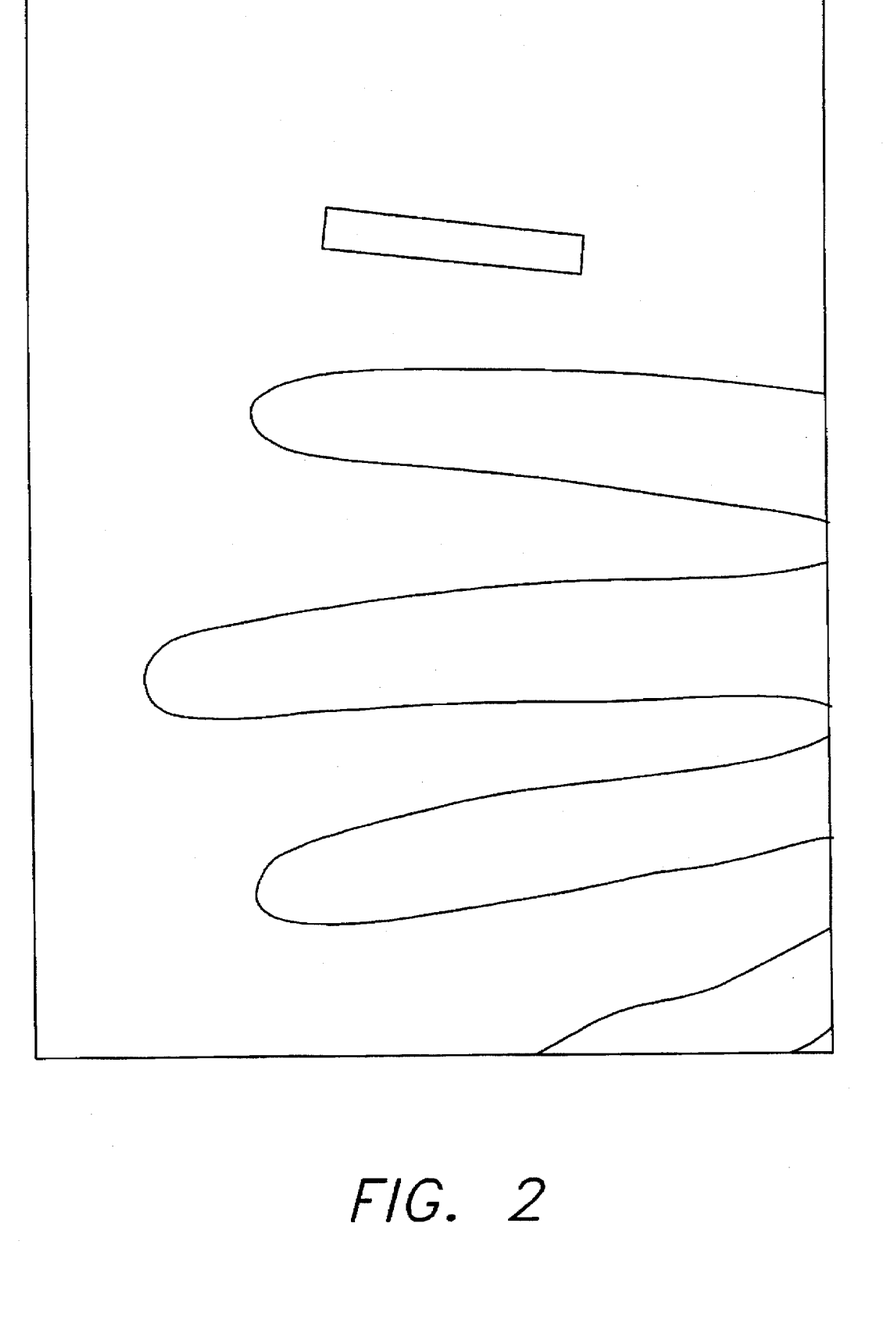
FIG. 2 shows the diagrammatic view of the binary thresholded version of FIG. 1.

The accurate estimate of upper and lower thresholds enables the effective binarization of the input gray scale image by a binarization system (Block 20). The result of this binarization yields a bi-tonal image. An example of this type of image is found in FIG. 2. Close inspection of FIG. 2 reveals a roughness of the edges between the foreground (hand) and background (film) regions. A noise removal system (Block 30) is used to smooth these edges and remove spot noise found elsewhere in the image. Straightforward morphological processing is the preferred method of noise removal.

Figure 3:
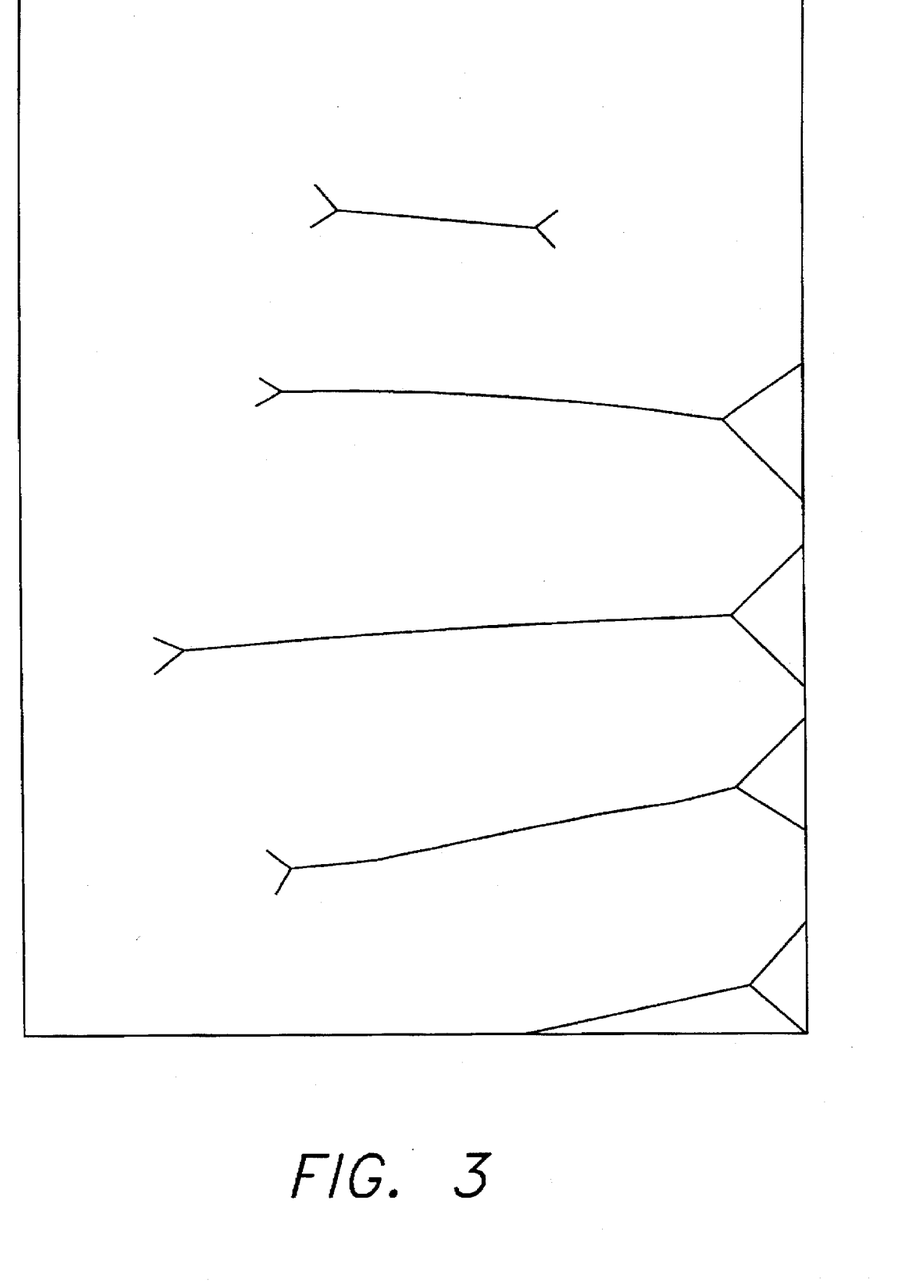
FIG. 3 shows the diagrammatic view of the medial axis transform of the binary image in FIG. 2.

The noise removed binary image is processed by a skeletonizing technique, such as a medial-axis transform (Block 40), or by the technique disclosed in U.S. patent application Ser. No. 07/739,649, in order to form an initial estimate of the central axis of each finger. FIG. 3 shows the result of the medial axis transfer.

Figure 4:
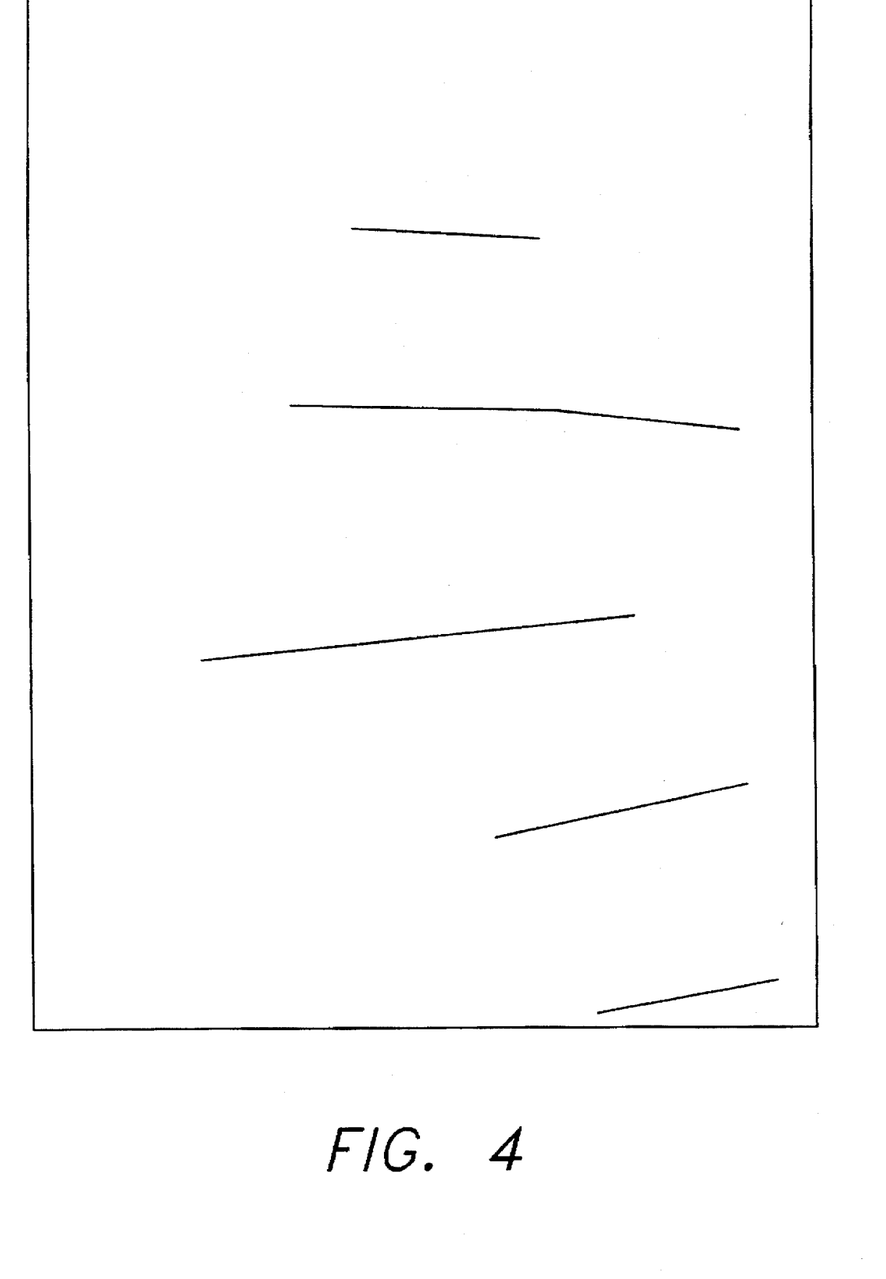
FIG. 4 shows the diagrammatic view of the linear approximation of the medial axis transform in FIG. 3. Small lines have been filtered out of FIG. 3 to perform this operation.

The locus of points generated by the medial axis transfer is approximated by a linear foot (Block 50). During this process, short lines and spurious points are discarded. The result of the linear fit is shown in FIG. 4. Note that this process occasionally results in multiple lines corresponding to the central axis for a given finger. This can be seen in the case of the index finger in FIG. 4, which is represented by two linear segments. A line linking system (Block 60) joins lines with near end points.

Figure 5:
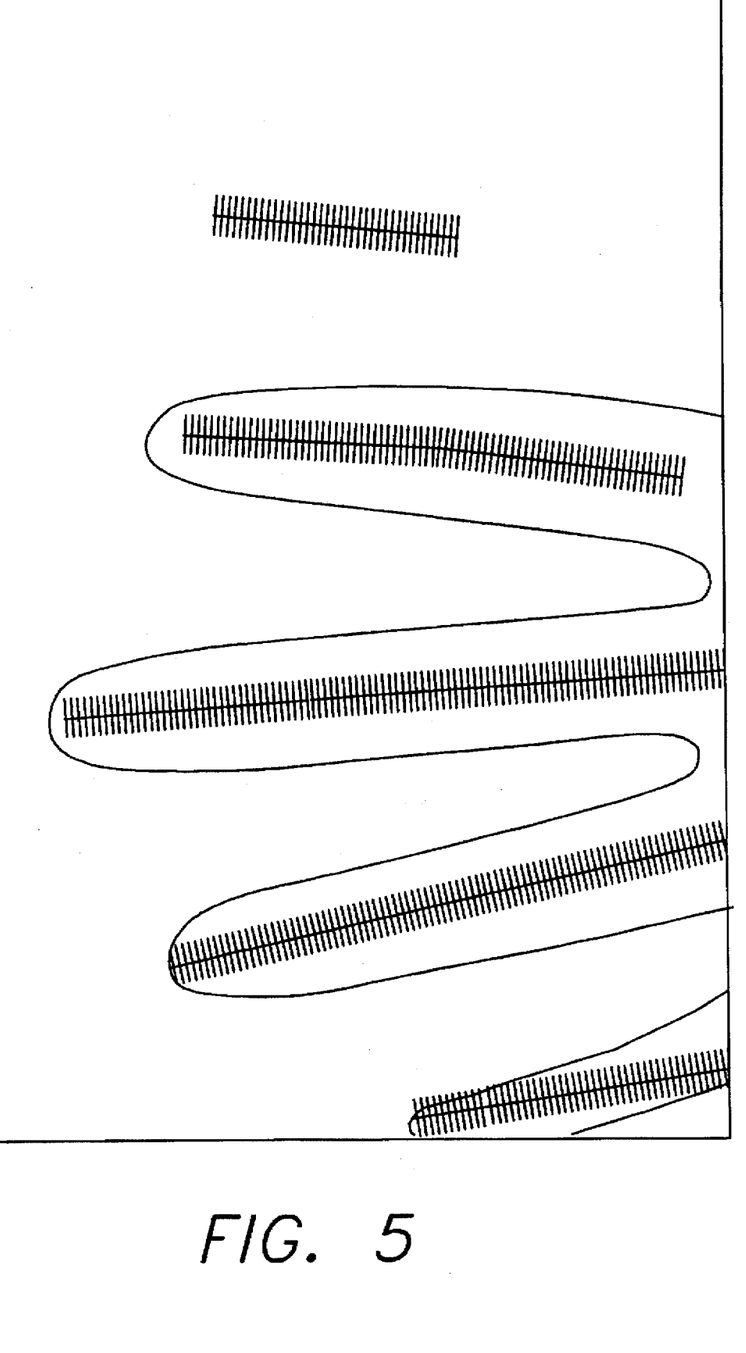
FIG. 5 shows the diagrammatic view of the adjusted linear approximations from FIG. 4. The ends of the linear approximation that lie near one another have been linked together to form a single piece wise linear approximation for each finger. The line ends of each linear approximation have been extended to ensure that each finger is fully traversed. The shorter crossing lines show the extent of the sampling used for trace generation.

The line linking system results in a piece wise linear approximation of the central axis for each finger. To that the axis traverses the entire length of the finger, the unlinked end points of each segment are extended until they encounter either an image boundary or a region identified as background by the binarization process. For each point along these axis, perpendicular projections are generated as illustrated in FIG. 5. The perpendicular projections are extended a fixed amount. The preferred embodiment currently extends the projections a 32 pixel distance on each side of the line. Pixel values along these perpendicular projections are used as sample points t estimate the density of the bone at their corresponding point on the axial segment.

Figure 6:
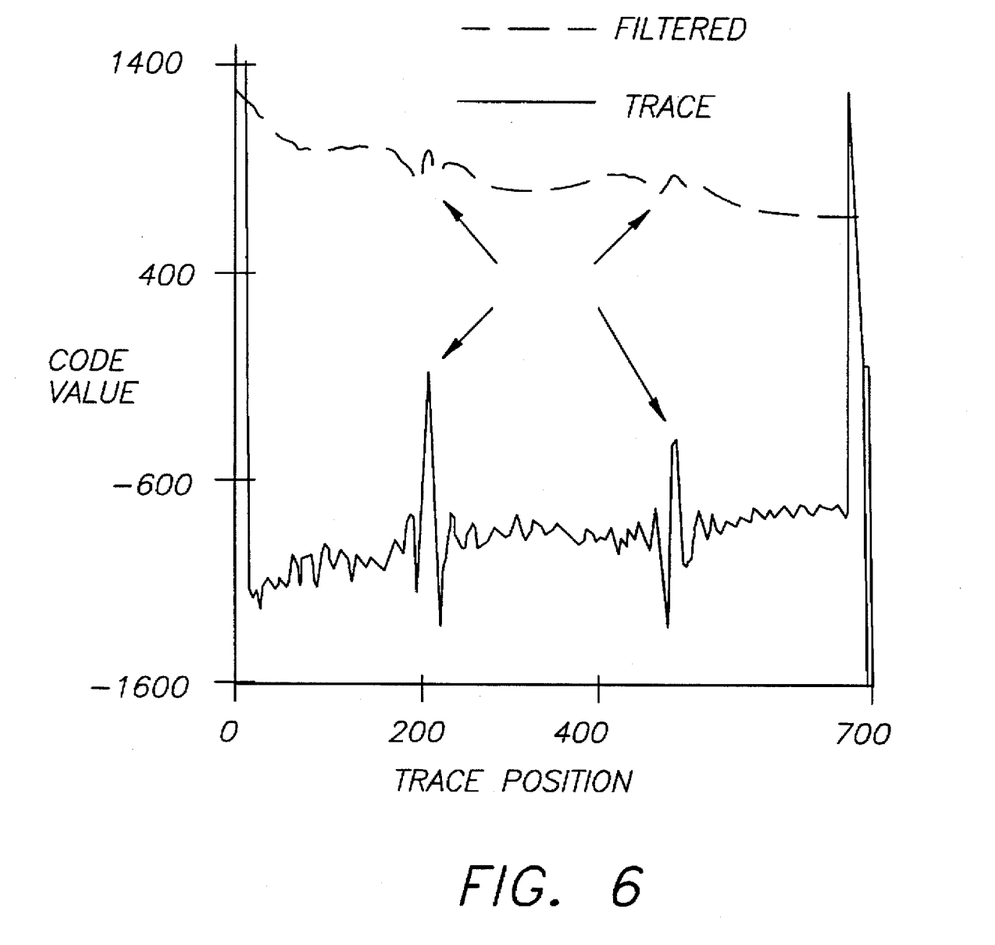
FIG. 6 shows a graphical view of code value vs. trace position of a typical trace generated from the locus of points shown in FIG. 5. The upper line of this graph shows the raw trace data each point corresponding to a unique point along the axial linear approximation of the finger. The lower line on the graph shows the upper line processed through a matched filter. Clearly, the joint locations are easily identified in as the two major spikes in the lower graph.

FIG. 5 shows perpendicular projections for only a fraction of the points along the axial segment. The preferred embodiment generates these projections for every point along the axial segments. The pixel values along a given perpendicular projection are averaged by a trace generation system (Block 80). The result of this trace generation system is seen as the upper line in FIG. 6.

In the preferred embodiment, the density traces are convolved with a matched filter (Block 90). The result of this operation is the lower trace in FIG. 6.

The output of the matched filter operation is analyzed by a joint detection system (Block 100). This system locates maximum points in the matched filtered trace. The search for maximum points is also constrained by the expected location of the joint points. The position of the standard wedge (Block 130) can be used to generate location estimates (Block 160) which can guide the search for potential joint locations in the image. This is possible because the standard wedge is preferably placed in approximately the same relative location to the fingers on every exam.

Figure 7:
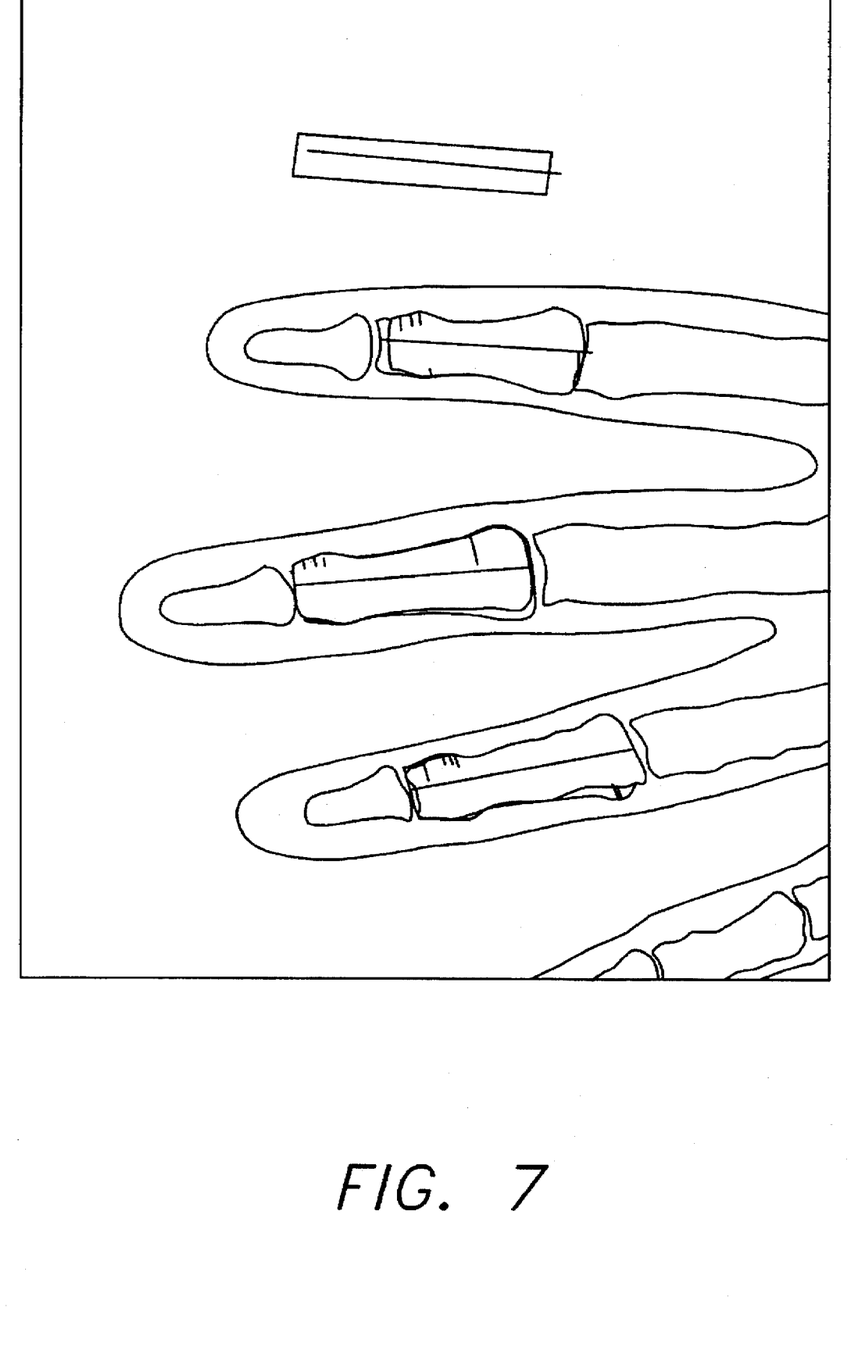
FIG. 7 shows a diagrammatic view of the segmented regions. These regions are delimited in extent by the joint position and the bone edge locations. Bone edges are determined through edge detection on traces perpendicular to the axial approximations.

Once the joint location for each of the three phalanges of interest has been determined. The bone edges are determined (Block 110) using the piece wise linear approximations of the axial lines which lie between the two joint locations. This is accomplished by generating perpendicular projections from the axial lines until the background region as determined by the threshold estimation system (Block 140) is encountered. Standard edge detection techniques are applied to the trace of density values generated by the perpendicular projections. The point of maximum edge determination which lies near the expected location of the edge is identified as the bone edge. The expected location of the edge is based on an approximate model of phalangeal shape which is easily derived because of the consistent anatomical shape of the phalanges. FIG. 7 shows the result of the bone edge detection. The area corresponding to the phalanges is clearly marked.

Average density values can be sampled from the areas shown in FIG. 7. These values can be processed in order to generate the average density of the bone (Block 170). Techniques for estimating risk from these density values are reported in the public domain (*Non-Invasive Measurements of Bone Mass and Their Clinical Application*, Cohn, S. H., ed. CRC Press, 1981).

The invention has been described in detail with particular reference to a preferred embodiment thereof, but it will be understood that variations and modifications can be effected within the spirit and scope of the invention.

Parts List 10 input image
20 binarization
30 noise removal
40 skeletonization technique
50 linear fitting
60 line linking
70 perpendicular projections
80 trace generation
90 matched filtering
100 joint detection
110 bone edge detection
112 region growing
114 labeling
120 shape analysis
130 wedge identification
140 threshold estimates
150 histogram analysis
160 location estimates
170 average density calculation
200 x-ray source
202 object
204 image acquisition system
206 scanner/digitizer
208 image processor
300 digital computer
310 memory
312 input device
314 display
426 central processing unit
318 output device
320 control/data bus
322 drive
324 storage media

What is claimed is:

1. A method of automatically segmenting the bone regions in a digital radiograph of a body extremity comprising the steps of:

providing a digital radiographic image of a body extremity having one or more digits;

estimating upper and lower threshold values of said provided image;

binarizing said provided image by a binarization system which uses said estimated upper and lower threshold values to produce a bi-tonal image;

removing noise from said bi-tonal image by a noise removal system;

processing said noise removed bi-tonal image by a skeletonization technique in order to form an initial estimate of the central axis of each body extremity digit;

approximating the locus of points generated by said processing step by a linear fit system;

joining lines with near end points with a line linking system which results in a piece wise linear approximation of the central axis for each body extremity digit;

for each point along the axes, generating perpendicular projections which extend a fixed pixel distance;

for each perpendicular projection, averaging the pixel values by a trace generation system;

convolving each density trace with a matched filter;

analyzing the output of said matched filter step by a joint detection system to locate digit joints;

for each body extremity digit, determining the bone edges between two joints; and determining the average density of the digit region between said digit joints and bone edges.

2. The method of claim 1 wherein said providing step provides a digital radiographic image of a hand and a standard wedge; wherein said estimating step includes the steps of estimating the upper and lower threshold values of the hand by a histogram analysis system and of estimating the upper and lower threshold value of said standard wedge by steps including region growing, labeling, shape analysis, wedge identification, and upper and lower threshold estimation and wherein said threshold values for said hand and said wedge are combined to determine optimal values for the upper and lower threshold.

3. The method of claim 2 wherein said combining step uses a weighted average of the two estimates for each threshold value.

4. The method of claim 1 wherein said noise removing step uses morphological processing to remove noise.

5. The method of claim 1 wherein in said processing step, short lines and spurious points are discarded.

6. The method of claim 1 wherein in said joining step, unlinked end points of each segment are extended until they encounter either an image boundary or a region identified as background.

7. The method of claim 1 including the step of generating the average density of the body extremity.

8. The method of claim 7 including the step of estimating the risk of osteoporosis based on said bone density values.

9. The method of claim 1 wherein said skeletonization technique used in said processing step is a medial-axis transform.

10. A computer storage product comprising:

a computer readable storage medium having a computer program stored thereon for performing a method of automatically segmenting the bone regions in a digital radiograph of a body extremity comprising the steps of:

providing a digital radiographic image of a body extremity having one or more digits;

estimating upper and lower threshold values of said provided image;

binarizing said provided image by a binarization system which uses said estimated upper and lower threshold values to produce a bi-tonal image;

removing noise from said bi-tonal image by a noise removal system;

processing said noise removed bi-tonal image by a skeletonization technique in order to form an initial estimate of the central axis of each body extremity digit;

approximating the locus of points generated by said processing step by a linear fit system;

joining lines with near end points with a line linking system which results in a piece wise linear approximation of the central axis for each body extremity digit;

for each point along the axes, generating perpendicular projections which extend a fixed pixel distance;

for each perpendicular projection, averaging the pixel values by a trace generation system;

convolving each density trace with a matched filter;

analyzing the output of said matched filter step by a joint detection system to locate digit joints;

for each body extremity digit, determining the bone edges between two joints; and determining the average density of the digit region between said digit joints and bone edges.

\* \* \* \* \*